United States Patent [19]
Lebkowski et al.

[11] Patent Number: 5,691,176
[45] Date of Patent: Nov. 25, 1997

[54] RECOMBINANT ADENO-ASSOCIATED VIRUS VECTOR PACKAGING CELLS AND METHODS FOR USE

[75] Inventors: Jane S. Lebkowski, Portola Valley; Maureen A. McNally; Thomas B. Okarma, both of Palo Alto, all of Calif.

[73] Assignee: Applied Immune Sciences, Inc., Menlo Park, Calif.

[21] Appl. No.: 459,091

[22] Filed: Jun. 2, 1995

Related U.S. Application Data

[62] Division of Ser. No. 236,642, May 2, 1994, abandoned, which is a division of Ser. No. 993,776, Dec. 21, 1992, Pat. No. 5,354,678, which is a continuation-in-part of Ser. No. 605,775, Oct. 30, 1990, Pat. No. 5,173,414.

[51] Int. Cl.[6] ............ C12N 15/00; C12N 7/01; C12N 15/35; C12N 5/06
[52] U.S. Cl. ............ 435/172.3; 435/235.1; 435/320.1; 435/325; 536/23.1
[58] Field of Search ............ 435/91.4, 235.1, 435/320.1, 69.1, 172.3, 366, 325; 424/93.21; 536/23.1

[56] References Cited

U.S. PATENT DOCUMENTS

| | | | |
|---|---|---|---|
| 4,686,186 | 8/1987 | Sugden | 435/243 |
| 4,797,368 | 1/1989 | Carter et al. | 435/320.1 |
| 5,173,414 | 12/1992 | Lebkowski et al. | 435/172.3 |

FOREIGN PATENT DOCUMENTS

WO 91/18088  11/1991  WIPO.

OTHER PUBLICATIONS

Lebkowski, J. et al., Mol and Cell. Biol.. vol. 8(10): 3988–3996, Oct. 1, 1988.
Samulski, R. J. et al.. J. Virol.. vol. 63(9): 3822–3828, Sep. 1, 1989.
Berns et al., *Advances in Virus Research*, 32:243–306 (1987).
Laughlin et al., *Gene*, 23:65–73 (1983).
Beaton et al., *J. Virol.*, 63(10):4450–4454 (1989).
Tratschin et al., *Mol. Cell. Biol.*, 4(10):2072–2081 (1984).
Tratschin et al., *Mol. Cell. Biol.*, 5(11):3251–3260 (1985).
Hermonat et al., *Proc. Natl. Acad. Sci.*, 81:6466–6470 (1984).
McLaughlin et al., *J. Virol.*, 62(6):1963–1973 (1988).
Samulski et al., *J. Virol.*, 63(9):3822–3828 (1989).
Lebkowski et al., *Mol. Cell. Biol.*, 8(10):3988–3996 (1988).
Dougherty et al., *J. Virol.*, 63(7):3209–3212 (1989).
Markowitz et al., *J. Virol.*, 62(4):1120–1124 (1988).
Clemens et al., *J. Virol.*, 63(6):2737–2745 (1989).
Mendelson et al., *Virol.*, 166:154–165 (1988).
Stary et al., *J. Virol.*, 63(9):3837–3843 (1989).
Tratschin et al., *Mol. Cell. Virol.*, 6(8):2884–2894 (1986).
Yates et al., *Nature*, 313:812–815 (1985).
Jalanko et al., *Biochem. Biophys. Acta*, 949:206–212 (1988).
Young et al., *Gene*, 62(2):171–185 (1988).
Mendelson et al., *Virol.*, 6(2):612–615 (1988).
Jalanko et al., *Gene*, 78:287–296 (1989).

(List continued on next page.)

*Primary Examiner*—David Guzo
*Assistant Examiner*—William Sandals
*Attorney, Agent, or Firm*—Synnestvedt & Lechner

[57] ABSTRACT

Simplified methods to produce recombinant adeno-associated virus (rAAV) vectors are described. The methods involve the use of chimeric plasmids which incorporate the Epstein Barr nuclear antigen (EBNA) gene, the latent origin of replication of Epstein Barr virus (oriP), and a rAAV genome. The chimeric plasmids themselves are also a part of the present invention. These plasmids are maintained as multicopy extra-chromosomal elements in cells, such as human 293 cells. Permanent cell lines carrying these EBV/AAV plasmids are induced to produce large amounts of rAAV upon addition of wild-type, adeno-associated virus helper functions. Vectors produced in this manner are capable of transducing exogenous genes into other human cell lines and exhibit the attributes of viral elements produced by conventional methods.

14 Claims, 9 Drawing Sheets

OTHER PUBLICATIONS

Konan et al., *Somatic Cell and Mol. Genetics*, 17(4):359–368 (1991).
Kotin et al., *Proc. Natl. Acad. Sci.*, 87:2211–2215 (1990).
Labow et al., *Mol. Cell. Biol.*, 7(4):1320–1325 (1987).
Labow et al., *J. Virol.*, 62:1705–1712 (1988).
Massie et al., *Mol. Cell. Biol.*, 6(8):2872–2883 (1986).
Ohi et al., *Gene*, 89:279–282 (1990).
Ruether et al., *Mol. Cell. Biol.*, 6(1):123–133 (1986).
Russell et al., *J. Virol.*, 66(5):2821–2828 (1992).
Samulski et al., *J. Virol.*, 61(10):3096–3101 (1987).
Trempe et al., *J. Virol.*, 62(1):68–74 (1988).
Weindler et al., *J. Virol.*, 65:2476–2483 (May 1991).
Laughlin, C.A. et al., *J. Virol.*, 41:868–876 (1982).
Muzyczka, N., *Curr. Top. Microbiol. Immunol.*, 158:97–129 (1992).
Berkner, K.L., *Biotechniques*, 6:616–624 (1988).

5,691,176

RECOMBINANT ADENO-ASSOCIATED VIRUS VECTOR PACKAGING CELLS AND METHODS FOR USE

This is a division of application Ser. No. 08/236,642 filed May 2, 1994, now abandoned which is a division of application Ser. No. 07/993,776,filed Dec. 21, 1992, now U.S. Pat. No. 5,354,678, which is a continuation-in-part of application Ser. No. 07/605,775, filed Oct. 30, 1990 now U.S. Pat. No. 5,173,414.

The invention was made with government support under the Department of Health and Human Services Public Health Service Small Business Innovation Research Program, Phase I Grant No.: 1R43CA56215-01. Accordingly, the government may have certain rights in the invention.

TECHNICAL FIELD

The present invention is directed generally to the field of genetic engineering and is particularly directed to the production of recombinant adeno-associated virus (AAV) vectors for use in transducing exogenous genes into mammalian, e.g., human cell lines.

BACKGROUND

Adeno-associated virus (AAV) is a single-stranded DNA parvovirus which is endogenous to the human population. Although capable of productive infection in cells from a variety of species, AAV is a dependovirus, requiring helper functions from either adenovirus or herpes virus for its own replication. In the absence of helper functions from either of these helper viruses, AAV will infect cells, uncoat in the nucleus, and integrate its genome into the host chromosome, but will not replicate or produce new viral particles.

The genome of AAV has been cloned into bacterial plasmids and is well characterized. The viral genome consists of 4682 bases which include two terminal repeats of 145 bases each. These terminal repeats serve as origins of DNA replication for the virus. Some investigators have also proposed that they have enhancer functions. The rest of the genome is divided into two functional domains. The left portion of the genome codes for the rep functions which regulate viral DNA replication and viral gene expression. The right side of the viral genome contains the cap genes that encode the structural capsid proteins VP1, VP2 and VP3. The proteins encoded by both the rep and cap genes function in trans during productive AAV replication.

AAV is considered an ideal candidate for use as a transducing vector, and it has been used in this manner. Such AAV transducing vectors comprise sufficient cis-acting functions to replicate in the presence of adenovirus or herpes virus helper functions provided in trans. Recombinant AAV (rAAV) have been constructed in a number of laboratories and have been used to carry exogenous genes into cells of a variety of lineages. In these vectors, the AAV cap and/or rep genes are deleted from the viral genome and replaced with a DNA segment of choice. Current vectors can accommodate up to 4300 bases of inserted DNA.

To produce rAAV, plasmids containing the desired viral construct are transfected into adenovirus-infected cells. In addition, a second helper plasmid is cotransfected into these cells to provide the AAV rep and cap genes which are obligatory for replication and packaging of the recombinant viral construct. Under these conditions, the rep and cap proteins of AAV act in trans to stimulate replication and packaging of the rAAV construct. Three days after transfection, rAAV is harvested from the cells along with adenovirus. The contaminating adenovirus is then inactivated by heat treatment.

Although the individual procedures currently used to make rAAV vectors are relatively simple, the processes suffer two drawbacks. Repeated transfection with the rAAV plasmid is required each time recombinant virus is to be made. Moreover, the production of rAAV virus is relatively inefficient due to the inherent inefficiency of cotransfecting two plasmids into a large proportion of cells. Accordingly, new procedures for the production of rAAV vectors are highly desirable.

Relevant Literature

For a general review of AAVs and of the adenovirus or herpes helper functions required, e.g., for their replication, see Berns and Bohensky (1987), "Adeno-Associated Viruses: An Update", *Advanced in Virus Research, Academic Press*, 33:243–306. The genome of AAV is described in Laughlin et al. (1983) "Cloning of infectious adeno-associated virus genomes in bacterial plasmids", *Gene*, 23: 65–73. Expression of AAV is described in Beaton et al. (1989) "Expression from the Adeno-associated virus p5 and p19 promoters is negatively regulated in trans by the rep protein", *J. Virol.*, 63:4450–4454. Construction of rAAV is described in a number of publications: Tratschin et al. (1984) "Adeno-associated virus vector for high frequency integration, expression and rescue of genes in mammalian cells", *Mol. Cell. Biol.*, 4:2072–2081; Hermonat and Muzyczka (1984) "Use of adeno-associated virus as a mammalian DNA cloning vector: Transduction of neomycin resistance into mammalian tissue culture cells", *Proc. Natl. Acad. Sci. USA*, 81:6466–6470; McLaughlin et al. (1988) "Adeno-associated virus general transduction vectors: Analysis of Proviral Structures", *J. Virol.*, 62:1963–1973; and Samulski et al. (1989) "Helper-free stocks of recombinant adeno-associated viruses: normal integration does not require viral gene expression", *J. Virol.*, 63:3822–3828. Cell lines that can be transformed by rAAV are those described in Lebkowski et al. (1988) "Adeno-associated virus: a vector system for efficient introduction and integration of DNA into a variety of mammalian cell types", *Mol. Cell. Biol.*, 8:3988–3996. "Producer" or "packaging" cell lines used in manufacturing recombinant retroviruses are described in Dougherty et al. (1989) *J. Virol.*, 63:3209–3212; and Markowitz et al. (1988) *J. Virol.*, 62:1120–1124.

SUMMARY OF THE INVENTION

It is an object of the present invention to provide techniques and genetic constructs useful for producing AAV recombinant vectors conveniently and in large quantities.

These and other objects of the invention have been accomplished by providing the vectors, cells and methods of the present invention.

One embodiment of the present invention provides AAV/ EBV plasmid vectors comprising: an Epstein Barr virus (EBV) nuclear antigen (EBNA) gene; an EBV latent origin of replication (oriP); and a preformed adeno-associated virus (AAV) transducing vector comprising exogenous genetic material and lacking a functional AAV rep gene, and preferably, also lacking a functional cap gene or genes. As used herein "cap gene" encompasses one or more of the genes encoding the cap proteins. Such plasmid vectors preferably also comprise a detectable marker gene, more preferably an antibiotic resistance gene, which may be located on the AAV vector portion of the plasmid, or elsewhere on the plasmid. Often, as a result of the manner in which such plasmids are commonly constructed, there are two different marker genes, one within and one outside the AAV vector portion of the plasmid.

The present invention further provides cells and cell lines comprising an AAV/EBV plasmid vector. Such cells or cell lines are useful in methods for producing rAAV. Such methods, as provided by the present invention, comprise the following steps.

Introducing into the rAAV producer cell an adenovirus vector comprising an AAV cap gene optionally under the control of an inducible promoter; and an AAV rep gene optionally under the control of an inducible promoter.

Introducing into a cell an AAV/EBV plasmid vector of the present invention to produce a rAAV producer cell.

Growing the rAAV producer cell in a cell growth medium.

Inducing expression of the AAV rep and cap genes, thereby producing a rAAV and isolating the rAAV.

Such a method may further comprise the step of infecting the rAAV producer cell with wild type adenovirus or herpes virus, or introducing into the transfected host cell a vector comprising adenovirus or herpes virus helper functions sufficient to permit AAV replication.

In order to produce rAAV, the rAAV producer cell line must be provided with adenovirus or herpes virus helper functions and the rep and cap genes. These have traditionally been supplied by wild type adenovirus and a plasmid containing the rep and cap genes of AAV.

The present invention, however, provides two alternative approaches to more efficiently produce rAAV from rAAV producer cells.

The first approach employs cells having stably incorporated in their genome one or more DNA sequences which together comprise the AAV rep and cap genes, and, preferably a detectable marker gene. Because the rep gene products may be toxic to certain cell lines, it is preferred that expression of the rep and cap genes be controlled by inducible promoters when the genes are introduced into these sensitive cell lines. The AAV/EBV vectors of the present invention are then introduced into such cells, and recombinant AAV is readily and efficiently produced by infection of the cells by a helper virus such as adenovirus or herpes virus. Once such a permanent producer cell line is produced, rAAV can be produced simply, e.g., by infecting the permanent producer cell line with adenovirus.

Thus, the present invention provides a method for producing rAAV comprising the following steps.

Introducing one or more DNA sequences into the genome of a cell, the sequences comprising an AAV rep gene optionally under the control of an inducible promoter and an AAV cap gene, optionally under the control of an inducible promoter, thereby producing a permanent packaging cell.

Growing the permanent packaging cell in a cell growth medium.

Inducing expression (if optional inducible promoters are used) of the cap and rep genes in the permanent producer cell and introducing adenovirus or herpes virus thereby producing rAAV and isolating the rAAV.

Introducing into the permanent packaging cell an AAV transducing vector lacking a functional AAV rep gene, preferably an AAV transducing vector of the present invention, thereby producing a permanent producer cell.

In the second approach, the AAV rep and cap genes are combined in a single recombinant adenovirus vector, i.e., a rep/cap adenovirus vector which combines in a single vector all complementing functions required for rAAV production. The rep/cap vectors of the present invention comprise: genes encoding helper functions, preferably from adenovirus, sufficient to permit AAV replication; and AAV cap and rep genes. In adenovirus rep/cap vectors the rep and cap genes may, for example, replace the adenovirus E3 gene or the adenovirus E1a and E1b genes.

Thus, in the second approach, rAAV is produced by a method comprising the following steps.

Introducing into a cell the genome of an AAV transducing vector of the present invention which lacks a functional AAV rep gene, and, preferably lacks a functional AAV cap gene as well; thereby producing a rAAV producer cell.

Growing the rAAV producer cell in a cell growth medium.

Introducing into the rAAV producer cell a rep/cap vector of the present invention, thereby producing a transfected producer cell.

Inducing the expression of the cap and rep genes in said transfected producer cell, thereby producing rAAV and isolating the rAAV.

In order to manipulate the host range and target cell specificity of rAAV, the present invention further provides AAV transducing vectors having the cellular tropism of a parvovirus other than AAV. Such vectors comprise a gene encoding a cap protein of the different parvovirus, e.g., MVM(p), and exogenous genetic material. Preferably, such an AAV/EBV plasmid vector comprises: an EBNA gene; an EBV oriP; and a preformed AAV transducing vector having the cellular tropism of a different parvovirus, wherein the AAV transducing vector comprises a gene encoding a cap protein of the different parvovirus and exogenous genetic material and lacks a functional AAV rep gene. Preferably, such vectors further comprise a detectable marker gene most preferably an antibiotic gene such as hygromycin or G418 resistance. Preferably, such vectors also lack one or more, and preferably all functioning AAV cap genes. Most preferably, the gene encoding the cap protein of the parvovirus is located on a rep/cap adenovirus vector.

The present invention further provides cells comprising such AAV transducing vectors with altered cellular tropisms. The present invention also provides methods for producing rAAV as described above, in which such AAV transducing vectors with altered cellular tropisms are employed in place of those having the wild type host range of AAV.

DESCRIPTION OF THE DRAWINGS

The present invention will be better understood by reference to the following detailed description of specific embodiments when considered in combination with the drawings that form part of the present specification, wherein.

DESCRIPTION OF THE SPECIFIC EMBODIMENTS

Figure 1:
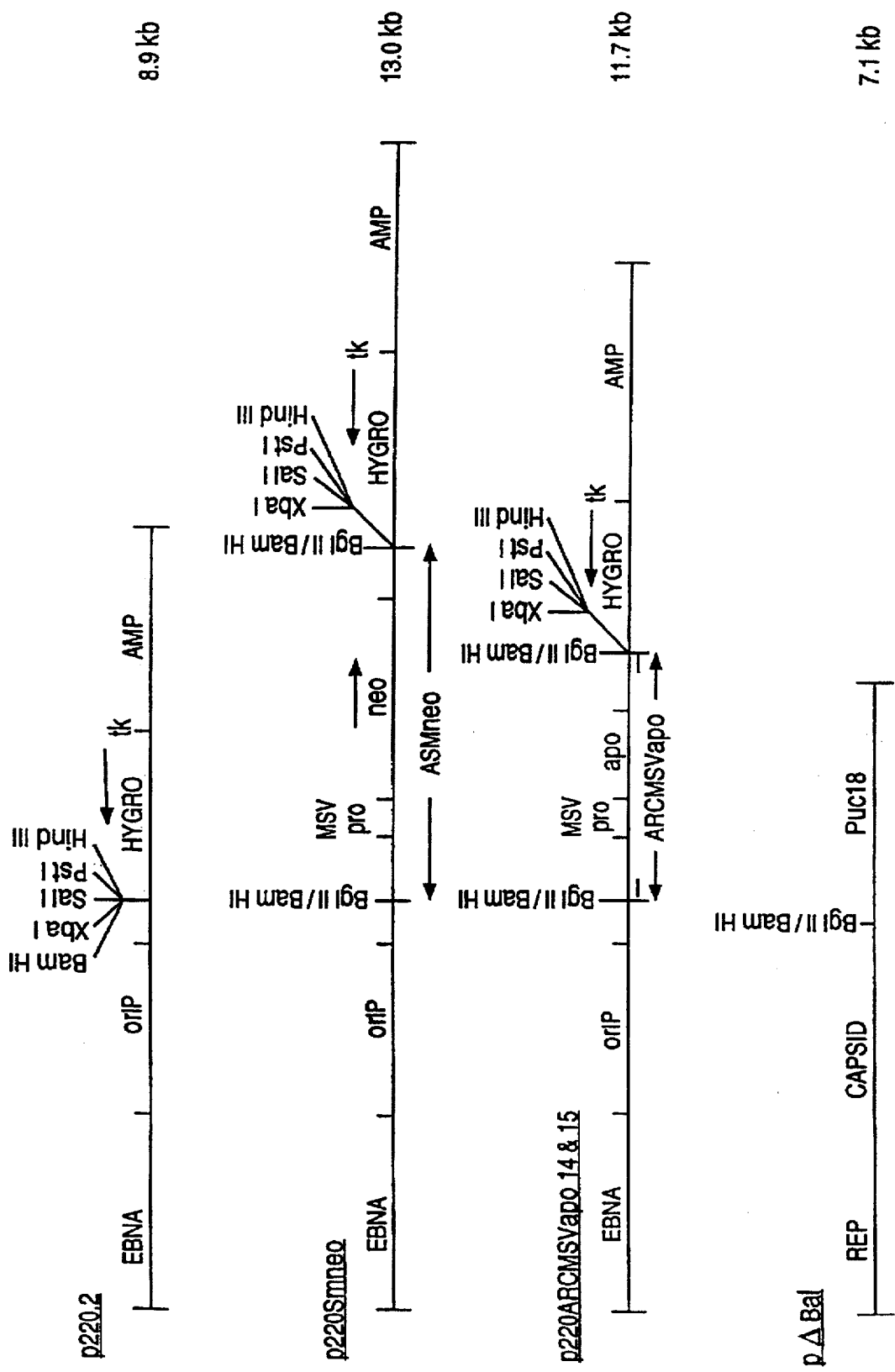
FIG. 1 is a schematic diagram of a number of plasmids that are either constructs of the invention or that are used to form constructs of the invention.

The present invention includes a new system to produce large amounts of rAAV vectors. The constructs used in the practice of the invention rely in part on the properties of Epstein Barr virus (EBV) plasmids which, in the presence of the EBV nuclear antigen (EBNA), remain as autonomously replicating plasmids in human cells. Although amplification of viral sequences using EBV vectors has previously been described, EBV plasmids have not been used in any system that generates a second virus vector, in this case the rAAV vector. Furthermore, there was no indication whether constructs containing sequences from both EBV vectors and AAV vectors would retain their desirable properties during cell reproduction or lytic production of virus.

In one method of the present invention, multiple copies of a rAAV genome are permanently established in human cells as part of a chimeric AAV/EBV plasmid. To produce large amounts of rAAV, these cells are infected with adenovirus or herpes virus (or appropriate recombinant constructs containing the required helper functions) and transfected with plasmids encoding any missing wild-type AAV rep or cap genes. Under these circumstances, lyric AAV replication ensues, and the amplified genomes are packaged as viable transducing vectors.

This method of producing rAAV vectors offers several advantages over conventional procedures for producing rAAV. Permanent cell lines containing a cloned rAAV genome may be used continually as a stable source of rAAV, obviating the need for relatively inefficient plasmid cotransfections every time rAAV virus is to be made. Accordingly, production of large quantities of AAV is more easily accomplished. Furthermore, recombinant EBV plasmids, once established in host cells, are stable structurally for at least three months, and lines containing intact copies of the chimeric plasmid can be screened. Newly transfected DNA, on the other hand, suffers a very high rate of point and rearrangement mutations, and viral production systems which rely on repeated transfection of recombinant virus genomes typically have a high frequency of mutant virus. This consideration is especially important if a recombinant virus is to be used in vivo in gene therapy protocols.

The present invention provides a chimeric AAV/EBV plasmid to maintain rAAV genomes at high copy number in a cell line permissive for efficient AAV reproduction; i.e., a good host for EBV plasmid vectors. This is in contrast to several studies which previously have reported that multiple copies of wild-type or rAAV integrate as tandem arrays into a fraction of infected Detroit 6 cells. See, Cheung et al., "Integration of the Adeno-Associated Virus Genome into Cellular DNA in Latently Infected Human Detroit 6 Cells", *J. Virol.*, 33:739–748. The integrated virus can be "rescued" from Detroit 6 cells upon adenovirus infection. Such a system could also be used as the starting point for the generation of rAAV. However, the present inventors have not observed tandem integration of AAV in host cells, such as human 293 cells, that are more useful in large-scale virus production. Only single copies of recombinant virus were observed in such cells, and viral "rescue" upon adenovirus superinfection was rarely seen. Therefore, the AAV/EBV chimeric vector system is more suitable for large-scale applications. With the system of the invention, production of cell clones containing multiple intact copies of the plasmid is efficient. Moreover, it allows the use of host cells, such as 293 cells, which are easily transfected and expressed and which produce large quantities of virus. While integration is possible, integrated vectors represent a less preferred aspect of the invention.

The original AAV/EBV chimeric vectors used in the development of the present invention contained rAAV genomes which were wild type for the viral rep proteins. In every case tested, these vectors failed to remain as plasmids in host cells, regardless of the orientation of the AAV construct within the EBV vector. Plasmid maintenance was only obtained when the wild-type rep functions were eliminated from the rAAV genome. In the presence of wild-type rep genes, the genes themselves or their encoded protein appear to have initiated EBV plasmid replication. Alternatively, they may have interfered with the expression of the EBNA functions encoded on the plasmid which are essential for plasmid maintenance. Such negative regulation of gene expression has been observed previously for other systems. However, recent evidence suggests that in some human cell lines, expression of rep may not be detrimental to cell viability. Alternatively, the rep gene could be placed under the control of an inducible promoter. In those cells sensitive to rep gene expression, it is preferred the rep gene be placed under the control of an inducible promoter.

rAAV produced using the AAV/EBV chimeric plasmids of the invention transduces genes with high frequency into human cells. In addition, these viral stocks so produced have undetectable levels of contaminating wild-type AAV. Although the methods described herein generate viral stocks with high titers of recombinant virus, higher titers are possible. As described here, the system provides for only the transient expression of AAV rep and cap genes in order to supply needed wild-type AAV functions. This situation can be optimized for the production of AAV cap proteins which are required stoichiometrically for the production of rAAV.

The method of invention can be carried out with a wide variety of host cells, generally any mammalian, preferably any human cell that can be infected by an Epstein Bart virus. Host cell lines are generally selected for ease of growth without complex media requirements, ease of drug selection of clones, high cloning efficiency, and maintenance of the highest possible EBV-AAV chimeric plasmid copy number. Example cell lines include 293, HeLa, KB and JW-22 cells. These cell lines are commonly available; for example, 293 cells, HeLa cells and KB cells are commercially available through the American Type Culture Collection. For instance, 293 cells, which are transformed primary human embryonal kidney cells, are available under the accession number ATCC CRL 1573.

The rAAV vectors of the present invention are readily constructed by those skilled in the art using conventional recombinant DNA techniques. Various techniques exist for eliminating a functional rep genetic region. Examples of typical genetic manipulations include deletions of genetic material in this region, insertions of genetic material that causes reading frame errors in this region, and point mutations that disrupt expression of the rep gene. Any AAV vector system can readily be tested for a functional rep gene by transfecting the construct into adenovirus-infected cells and examining their extracts 48 hours later for the presence of replicating vector genomes. If a wild-type rep gene is present, replicating DNA will be apparent on Southern blots prepared from the cell extracts.

There are relatively few limitations on the rAAV vector. The complete AAV genome should not exceed 4700 base pairs. The two terminal repeats (origins of replication) of AAV must be present in the construct. There is no limitation on the nature of the exogenous genetic material that is included in the recombinant plasmid vector.

The recombinant AAV/EBV vectors of the present invention comprise, a rAAV vector and an effective amount of EBV DNA defined as sufficient genetic material from EBV to allow the recombinant plasmid to function in the manner described herein. Minimally, this includes a genetic region encoding EBNA and an EBV oriP. Other regions of EBV can be present, but are not required.

The recombinant rep/cap adenovirus vectors of the present invention, as described below in Example 7, contain the rep and cap genes of wild type AAV and all elements of adenovirus required in trans to produce rAAV. Alternatively, elements required in trans (i.e., E1a and E1b) may be deleted and subsequently supplied by the host cell line. For example, 293 cells are useful for this purpose since they express E1a and E1b constitutively.

Alternatively, the rep and cap genes may be stably integrated into the genome of the cell line.

The recombinant vectors of the present invention may be introduced into host cells by any of the conventional means well known in the art, e.g., by transfection methods described previously for transforming cells with EBV. Likewise, the process of growing transfected cells in a cell growth medium is conventional. Once cells have reproduced to the desired level, the host cells are infected with adenovirus or herpes virus, and/or transfected with a plasmid or other vector containing wild-type AAV helper functions. It is within the ability of those skilled in the art to construct recombinant plasmids containing the adenovirus or herpes virus helper functions by recombinant DNA or genetic methods.

Additionally, it is necessary to provide any missing AAV genes, such as those encoding rep or cap proteins, that have been deleted from the AAV recombinant vector. This is typically done by transfecting the host cell line with a plasmid containing the appropriate genetic material, which may include cap genes or portions thereof from parvoviruses other than AAV in order to alter the host specificity of the rAAV, as described in greater detail in Example 8 below.

Specific examples of the individual steps described above are set forth in the following examples. However, it will be apparent to one of ordinary skill in the art that many modifications can be made, and that the examples are provided for purposes of illustration only and are not limiting of the invention unless so specified.

EXAMPLE 1

Plasmid Constructions

All DNA manipulations and plasmid constructions were performed using standard procedures. The plasmid pBal was constructed as described by Lebkowski et al. (1988). Two different rAAV constructs were cloned into the EBV plasmid p220.2, as shown in FIG. 1. Plasmid p220.2 contains the gene encoding EBNA and the EBV oriP DNA fragment which serves as the latent origin of replication of the virus. Yates et al. "Stable Replication of Plasmids Derived from Epstein-Barr Virus in Various Mammalian Cells", Nature, 313:812–815 and Sugden et al. "A Vector That Replicates as a Plasmid and Can Be Efficiently Selected in B-lymphoblasts Transformed by Epstein-Barr Virus", Mol. Cell. Biol., 5:410–413). The plasmid also contains the hygromycin B resistance gene to allow selection of transformants with high frequency. In the drug resistant transformed cells, p220.2 is maintained as a autonomously replicating unit at approximately 10–100 copies per cell.

The chimeric AAV/EBV vector constructions are shown in FIG. 1. p220ASMneo was constructed by inserting the partial BglII fragment from pSMneo, an exemplary, previously known, rAAV vector, into the BamHI polylinker site of p220.2. Likewise, the rAAV vector ARCMSVapo was cloned into p220.2 to form p220ARCMSVapo 14 and 15. Subclones 14 and 15 denote the two different orientations of ARCMSVapo in p220.2.

To construct p220ARCMSVapo 14 and 15, pARCMSVapo was used as an intermediate. Briefly, pARCMSVapo was constructed by inserting into pASHK a HindIII-KpnI fragment containing an apo A1 cDNA clone. The Murine sarcoma virus (MSV) and long terminal repeat (LTR) were then inserted into the HindIII site of this plasmid to yield pARCMSVapo. To construct p220ARCMSVapo, the rAAV vector was cleaved from pARCMSVapo with BglII and inserted into the BamHI site of p220.0.

EXAMPLE 2

Cells: growth and maintenance

Human 293 cells (ATCC CRL 1573), were maintained in Dulbecco's modified Eagle's medium (DMEM) containing 10% fetal calf serum (FCS) and 100 U/ml penicillin and streptomycin. Cells were grown in a humidified 37° C. incubator supplemented with 5% $CO_2$. Selection of hygromycin B resistant 293 cells usually started 3–5 days after transfection with AAV/EBV chimeric plasmids.

K562 cells were grown in RPMI containing 10% FCS and 100 U/ml penicillin and streptomycin. K562 cells were infected with rAAV stocks as described by Lebkowski et al. (1988), except that $1\times10^6$ K562 cells were incubated with 5 ml of any given viral stock. Viral infection efficiencies were determined by monitoring G418 resistance frequencies in the manner described by Lebkowski et al. (1988).

To start the drug selection process, the culture medium was withdrawn from the cells and fresh medium containing either 200 μg/ml hygromycin B or 1 mg/ml G418 was added. The procedure was repeated every 2–3 days until the selection process was complete. 293 cells containing chimeric AAV/EBV plasmids were constantly maintained in culture medium containing the appropriate selective drug.

EXAMPLE 3

Transfection of Cells with Recombinant Plasmids and Evaluation of Transfected Cells All three AAV/EBV chimeric vectors described in Example 1 were transfected into human 293 cells, and stable drug-resistant cell lines were selected. 293 cells containing p220ARCMSVapo 14 and 15 were selected in the presence of hygromycin B, whereas cells transformed by p220SMneo were selected using the drug G418 as described in Example 2. Individual drug-resistant clones containing each construct were grown to mass culture and used for experimentation. Pools of greater than 100 individual 293 cell clones were also made to represent a population of drug resistant clones. These pools are referred to as "populations."

Cells transformed by the three AAV/EBV constructs were examined for autonomously replicating chimeric plasmid. In these experiments, small molecular weight DNA was extracted from selected cell lines using the procedure described by Hirt (1967) "Selective Extraction of Polyoma DNA From Infected Mouse Cultures", *J. Mol. Biol.*, 126:275–288. The extracted DNA was introduced into *Escherichia coli* strain HB101, and transformed bacteria were selected in the presence of ampicillin. Plasmid DNA was isolated from cultures inoculated with individual bacterial colonies and was characterized by restriction enzyme analysis on polyacrylamide gels.

Plasmid p220SMneo could be rescued from G418-resistant 293 cells and reintroduced into *E. coli*. The plasmid DNA that was isolated from individual bacterial colonies transformed with small molecular weight DNA from 7 individual and one population of p220SMneo 293 cells could be seen on the gels. At the time of the Hirt extraction, these G418 resistant 293 cells had been in culture for over 2 months. In all instances, HindIII restriction analysis of the isolated plasmids yielded DNA fragments of the expected length of 0.5, 2.8 and 9.7 kb. Such results indicate that p220SMneo was maintained as a plasmid in the G418-resistant 293 cells. The rescued plasmids were also identical in size and restriction analysis to the original p220SMneo, suggesting that the plasmid did not undergo major rearrangements during its residence in the mammalian cells. These observations were verified by Southern blot analysis of HindIII-restricted, small molecular weight DNA isolated from the various G418-resistant 293 cells.

Similar analysis was performed on hygromycin-B-resistant 293 cell clones and populations that were generated using the plasmids p220ARCMSVapo 14 and 15. As above, this analysis was performed on hygromycin-B-resistant 293 cells that had been in culture for over 2 months. The HindIII restriction digests of plasmid DNA isolated from bacterial colonies transformed by small molecular weight DNA from hygromycin-resistant 293 cells could be seen in the gels, as could the plasmid rescued from two p220ARCMSVapo15 293 cell clones. Again, in all of the cases, intact plasmid could be rescued from the p220ARCMSVapo 14 and 15 293 cells. In one instance, in clone 15-3, an additional deleted version of p220ARCMSVapo 15 was also observed, believed to represent a deletion which occurred shortly after transfection.

To date, such analysis has been performed on 10 clones and 2 populations of drug-resistant 293 cells produced by p220SMneo and on 3 clones and 2 populations produced by p220ARCMSVapo 14 and 15. In all instances, unrearranged plasmid could be rescued from the mammalian cells even after two months in culture. Moreover, in 15 out of 17 drug resistant cell lines tested, only unrearranged plasmid was observed. For one of the 293 cells clones, referred to as neoC', the p220SMneo plasmid has been retrieved three months after the establishment of the clone and the plasmid structure has been examined from 36 transformed bacterial colonies. In each case only un-rearranged plasmid was observed. This result indicates that the AAV/EBV chimeric vectors are stably maintained in 293 cells for a period of at least three months.

The above data are consistent with plasmid maintenance of the chimeric AAV/EBV vectors. In this situation, the chimeric plasmid replicates along with the host chromosome, presumably using the oriP region of EBV as its origin of replication.

EXAMPLE 4

Production of rAAV virus

In order to determine whether a switch to lytic AAV replication would ensue if the appropriate AAV helper factors were supplied, we performed the following experiment. Human 293 cells containing AAV/EBV chimeric vectors were plated out 2 days before virus generation into fresh medium lacking hygromycin B. These cells were seeded into cultures such that on the day of virus production, the cells were approximately 25–40% confluent on 100-mm culture dishes. To produce recombinant virus, these cells were infected with adenovirus 2 stocks (multiplicity of infection of 1 to 5) for 2–4 hours. The cells were then transfected with 20 μg pBal using calcium phosphate mediated coprecipitation according to the method described by Wigler et al., "Transformation of Mammalian Cells with Genes From Procaryotes and Eukaryotes", *Cell*, 16:777–785. The next day the medium was withdrawn and replaced with 5 ml of fresh medium lacking hygromycin B. Two days later, the cytopathic effect of adenovirus was evident, and rAAV virus stock was harvested.

To harvest virus, the cells and medium were collected, and the cells were completely lysed by two 1-sec pulses of sonication. The viral stock was cleared of cellular debris by centrifugation and adenovirus was inactivated by heating the stock at 56° C. for one hour. Before use, the stock was filtered through a 1 micron cellulose acetate membrane.

Small molecular weight DNA was collected from cells using the procedure of Hirt (1967). This DNA was purified by treating the Hirt lysate with 10 μg/ml proteinase K followed by sequential extractions with phenol and phenol:chloroform: isoamyl alcohol (25:24:1). The purified DNA was then concentrated by ethanol precipitation and used as described. For Southern blots, the DNA was run on 0.8% agarose gels and blotted onto nylon membranes according to the manufacturer's instructions (Hybond N+; Amersham). The blots were probed with DNA fragments labeled by the random priming method according to the manufacturer's instructions (Pharmacia, Piscataway, N.J.). After aqueous hybridization at 65° C., the filters were washed at 65° C. with solutions of increasing stringency concluding with 0.1×SSC (15 mM NaCl, 1.5 mM sodium citrate pH 7.0,)+1.0% SDS. Autoradiograms were produced by exposure to X-ray film (type XAR; Eastman Kodak Co. Rochester, N.Y.).

For the analysis of the episomal nature of chimeric AAV/EBV plasmids in 293 cells, small molecular weight DNA was isolated from cells using the Hirt procedure as described above and transformed into *E. coli* strain HB101. Small-scale preparation of plasmid were purified from 1 ml cultures of single bacterial colonies. Plasmid characterization was performed by restriction enzyme analysis.

The results obtained showed that when cells containing p220ARCMSVapo 14 or 15 plasmid were infected with adenovirus and transfected with pBal, lytic replication of the AAV construct began. This event was evidenced by the appearance of a 2.8 kb band which hybridizes to an apoA1 probe. This 2.8 kb band is the correct size for the recombinant ARCMSVapo genome cloned into p220ARCMSVapo 14 and 15. Also visible was a ladder of faint bands starting at 5.6 kb. These bands represent multimers of the rAAV genome which are known to be intermediates in AAV replication.

The appearance of the 2.8 kb rAAV genome is completely dependent on the presence of wild-type AAV helper functions. If these same cells were simply infected with adenovirus or infected with adenovirus and transfected with the rep deletion mutant pSCap, no ARCMSVapo replication was observed. Moreover, the amplification of the rAAV construct was dependent on the presence of the AAV/EBV chimeric plasmid. Parental 293 cells which lack the AAV/EBV chimeric vector showed no ARCMSVapo amplification even in the presence of both wild type AAV functions. To date, a total of six p220ARCMSVapo14 and eleven p220ARCMSVapo15 clones have been tested. In every instance, replication of the rAAV construct occurred when the cells were supplied with adenovirus and wild-type AAV functions. Moreover, such amplification did not depend on the orientation of the rAAV construct in the EBV vector. Both orientations led to similar levels of ARCMSVapo amplification.

Lyric replication of the rAAV construct can also be initiated in cell clones containing p220SMneo. Again, replication of the rAAV construct was dependent on the simultaneous presence of adenovirus and wild-type AAV functions. p220SMneo cell clones which have been simply infected with adenovirus do not contain sequences of the recombinant ASMneo size. Similar results were observed if these cells were infected with adenovirus and transfected with the rep mutant pSCcap. However, if these adenovirus infected clones were provided both the AAV rep and cap genes from pBal, lyric replication of ASMneo occurred as detected by the appearance of a 4.1 kb band which hybridized with the neomycin phosphotransferase gene. This 4.1 kb fragment is the expected size of the recombinant ASMneo genome. Again, 293 cells which do not contain the chimeric plasmid do not show the appearance of the 4.1 kb band under any circumstances. Therefore, replication of a rAAV vector can occur from the two different chimeric AAV/EBV plasmid types tested and indicates that this phenomenon is applicable to a wide variety of constructs.

EXAMPLE 5

Analysis of transfected cells for recombinational events

The AAV constructs in p220ARCMSVapo14, 15, and p220SMneo have all but 1350 bases of wild-type AAV DNA deleted. They are defective for both the rep and cap functions of AAV. The plasmid pBal, which is used to supply the rep and cap AAV functions, is wild type for all AAV sequences except for deletions of 121 bases in each 145 base terminal repeat. As a result, the AAV construct in pBal is defective for the cis functions necessary for AAV viral replication. One important question in these studies was whether recombinational events occur between the constructs and pBAL during rAAV replication sufficient to generate replicating wild-type AAV genomes.

To answer this question, cell clones containing either p220ARCMSVapo14, 15, or p220SMneo were infected with adenovirus and transfected with pBal. Forty-eight hours later, Hirt extracts of these transfectants were made and analyzed for the presence of rAAV and wild-type AAV sequences.

As outlined above, such treatment of the AAV/EBV chimeric vector cell clones induces amplification of the rAAV construct as evidenced by the appearance of the appropriate recombinant genomes of 2.8 and 4.1 kb. When these same Southern blots were reprobed with the AAV capsid gene, no bands corresponding to the 4.7 kb, wild-type genome were observed. The only hybridizing sequences sometimes observed correspond to those from residual pBal plasmid DNA remaining in the cells after transfection. Support for this conclusion comes from the observation that these residual super-coiled, nicked, and linear pBal bands can also be observed after identical treatment of parental 293 cells. Therefore, during the greater than 10,000-fold amplification of the rAAV construct, no detectable production of the wild-type genome was observed.

EXAMPLE 6

Analysis of rAAV virus produced by the method of the invention

Viral stocks produced from p220SMneo cell clones infected with both adenovirus and pBal were tested for the presence of transducing recombinant ASMneo virus. In these experiments, K562 cells, from a human leukemia line, were infected with pASMneo and selected for the presence of the neomycin phosphotransferase gene. Table 1 shows the results of three such experiments. Table 1. Infection Efficiencies of rAAV Stocks.

TABLE 1

| 220SMneo | Infection Efficiencies of rAAV Stocks. | | |
|---|---|---|---|
| | % of K562 Cells Infected | | |
| Cell Line | EXPT 1 | EXPT 2 | EXPT 3 |
| clone1 | 0.04 | — | — |
| clone2 | — | 0.03 | — |
| clone3 | 0.5 | — | — |
| clone4 | 0.7 | 1.0 | — |
| clone5 | 0.0 | 0.0 | — |
| population1 | 0.8 | 0.0 | — |
| cloneA' | — | — | 0.15 |
| cloneB' | — | — | 0.10 |
| cloneC' | — | 0.05 | — |
| cloneD' | — | — | 0.10 |
| population1' | — | — | 1.0 |

Ten of the eleven of the cell lines tested produced rAAV which was capable of infecting K562 cells and stably producing G418 resistant K562 clones. Infection efficiencies varied somewhat from experiment to experiment ranging from 0 to 1.0%. There was also some variability in the viral titers of stocks produced from the various p220SMneo cell clones. For instance, recombinant virus stocks produced from cell lines 220SMneo4 routinely produced higher infection efficiencies than those from the other cell clones.

Recombinant virus produced from p220SMneo and p220ARCMSVapo15 clones are also capable of coinfection. K562 cells were coinfected with ASMneo and ARCMSVapo stocks that were produced as described as above. G418 resistant clones were selected, pooled, and screened for the secretion of apolipoprotein A1. In one such experiment, these and control K562 cells were labeled with $^{35}$S-methionine, and the cell culture supernatant was immunoprecipitated with a polyclonal anti-apoA1 antibody. Briefly, coinfected cells were labeled for 4 days in standard medium containing 200 µCi $^{35}$S-methionine. At this point, the culture medium was cleared of cells by centrifugation and incubated with 100 µl of protein-A-conjugated agarose beads (Repligen) which had been previously coated for 3 hours with an excess of anti-human apolipoprotein A1 rabbit antiserum (Boehringer Mannheim). The cell culture medium bead mixture was incubated overnight at 37° C. using gentle rotation. The following morning, the beads were collected and washed two times by centrifugation. Bound proteins were released using Laemmli sample buffer and analyzed on 15% SDS/PAGE gels according to the method of Laemmli (1970) Nature, 227:680–685. Cell culture proteins which were immunoprecipitated were visualized by autoradiography of the dried gel.

Analysis of the immunoprecipitates indicates that apolipoprotein A1 was secreted from the cells coinfected with the two viral stocks. Control K562 cells did not secrete this protein. These combined experiments indicated that rAAV virus produced by this simplified method can be used to easily transduce one or two genes into single cells. In the context of these vectors, the transduced genes are properly expressed and their proteins appropriately targeted to various cell compartments.

EXAMPLE 7

Figure 2:
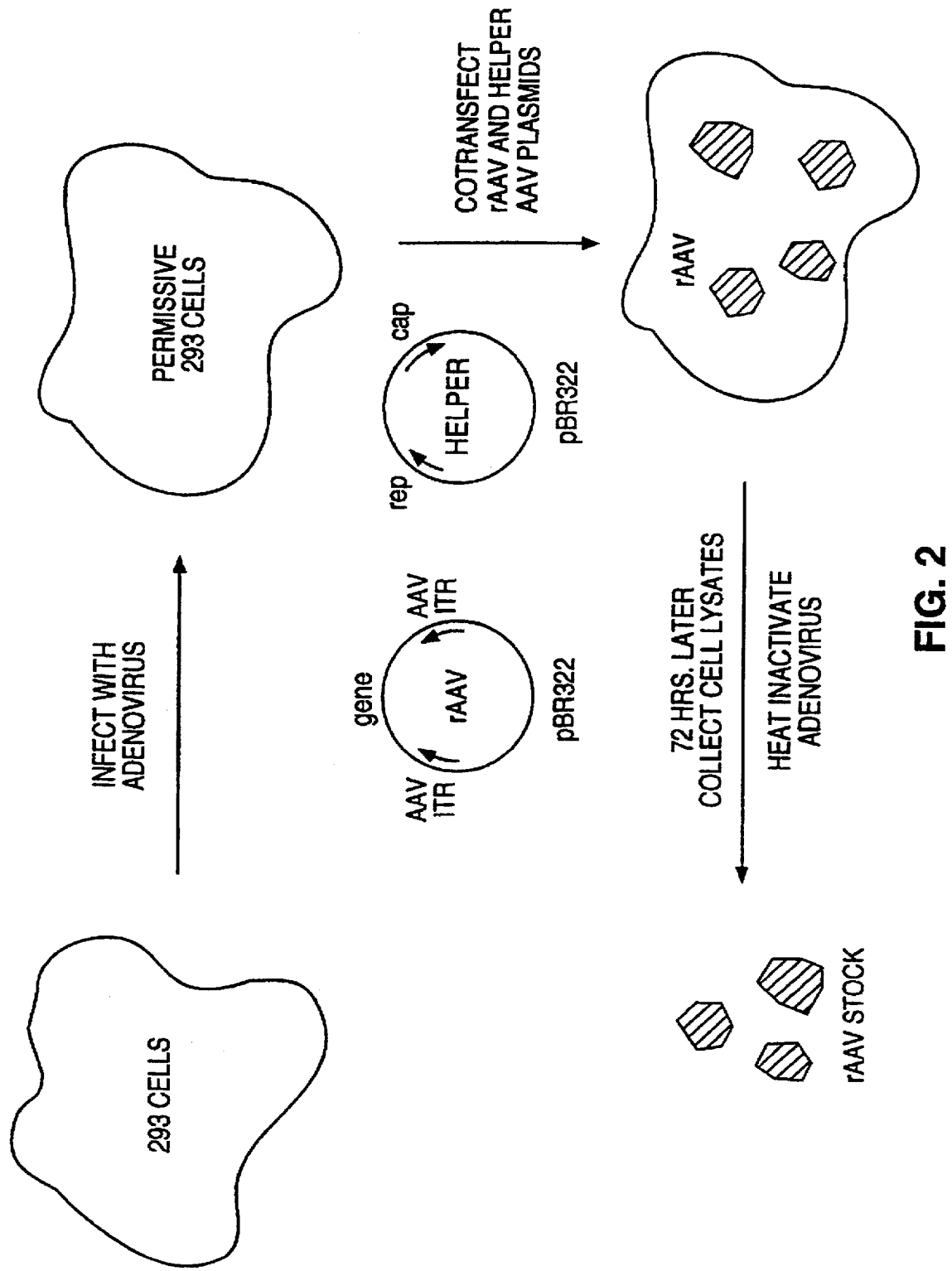
FIG. 2 shows the steps by which rAAV is produced by conventional methods.
Figure 3:
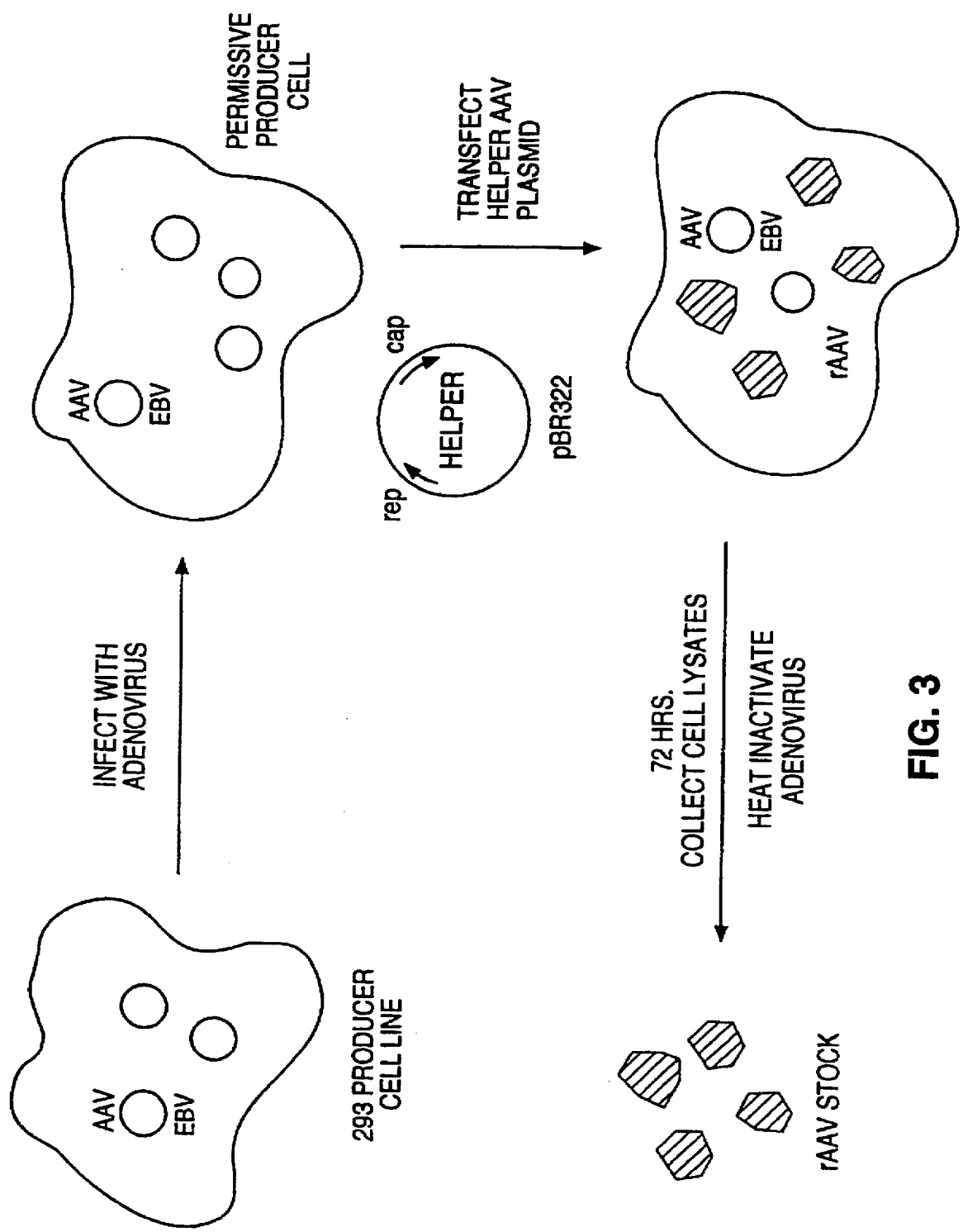
FIG. 3 shows the steps by which recombinant AAV is produced from a 293 producer cell line containing an AAV/EBV plasmid.

Construction of efficient systems to deliver wild type AAV rep and cap functions to the rAAV producer cell line In order to produce rAAV virus from cell lines, the cell lines must be infected with adenovirus and cotransfected with the rep and cap genes of AAV and with a rAAV vector, e.g., a AAV/EBV vector of the present invention, as shown in FIG. 2. Alternatively, rAAV producer cell lines may be used, but there remains a need for infection and transfection steps, as shown in FIG. 3. Even with the best transfection procedures, however, only approximately 1–10% of the target cells are productively transfected.

A permanent packaging cell line which expresses the AAV rep and cap genes may eliminate the need for the transfection step. Moreover, since every transformed cell expresses the rep and cap genes, production of rAAV is maximized.

Two different approaches are employed in order to introduce the rep and cap genes into a producer cell line.

First, a rAAV permanent packaging cell line which has the rep and cap genes permanently incorporated in its genome is produced by individually transfecting the rep and cap genes of AAV along with a selectable marker into 293 cells. Expression of the two rep genes is driven by an inducible transcriptional promoter, such as the mouse mammary tumor virus (MMTV) LTR or the metallothionein promoter. The inducible promoter chosen for construction of the rAAV producer cell lines should not be leaky, because the constitutive expression of rep may be toxic to mammalian cells.

Successfully transfected 293 cell clones are selected and screened. A transfected cell line is chosen on the basis of the production of high levels of the cap proteins and inducible expression of the rep genes and used as a recipient for the AAV-EBV chimeric plasmids. High level expression of both the cap and rep genes is initially screened by amplification of their mRNAs by reverse transcriptase RNA PCR. The PCR results are confirmed by immunoprecipitation of cell lysates by anti-capsid and anti-rep antibodies. The final test of these cell lines involves a functional test which measures production of rAAV.

Figure 4:
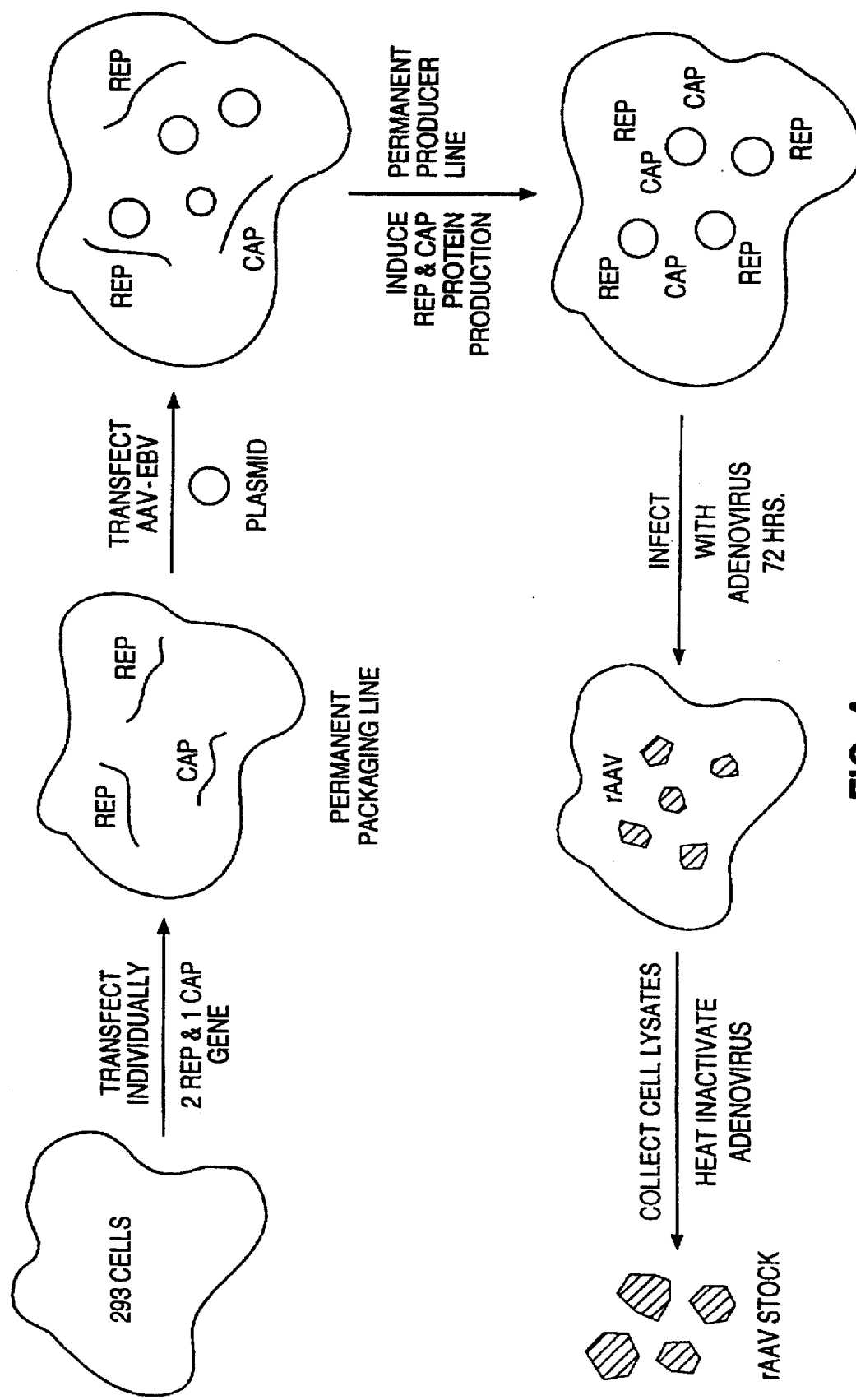
FIG. 4 shows the steps by which recombinant AAV is produced by a 293 permanent producer cell line having AAV rep and cap genes incorporated in its genome and containing an AAV/EBV plasmid.

Clones which contain the AAV/EBV chimeric plasmid are selected and reanalyzed for rep and cap gene expression. The resulting rAAV permanent producer cells express the rep and cap genes when properly induced and have multiple permanent copies of an rAAV genome. Therefore, simple and efficient adenovirus infection of induced producer cells results in production of the rAAV. FIG. 4 depicts a flow diagram illustrating the steps listed above. The titer of rAAV produced varies widely depending on the actual virus produced, but is typically high, i.e., above $10^4$ rAAV/ml. The cells are analyzed for the presence of: (1) replication of rAAV genomes; (2) transducing rAAV; and (3) wild type AAV, by standard molecular biology and tissue culture procedures.

As a second approach, the rep and cap genes are incorporated in a recombinant adenovirus vector to form a rep/cap adenovirus vector which can efficiently deliver genes to human cells. Ruether et al. (1986) *Mol. Cell. Biol.*, 6:123–133; and Massie et al. (1986) *Mol. Cell. Biol.*, 6:2872–2883.

Figure 5:
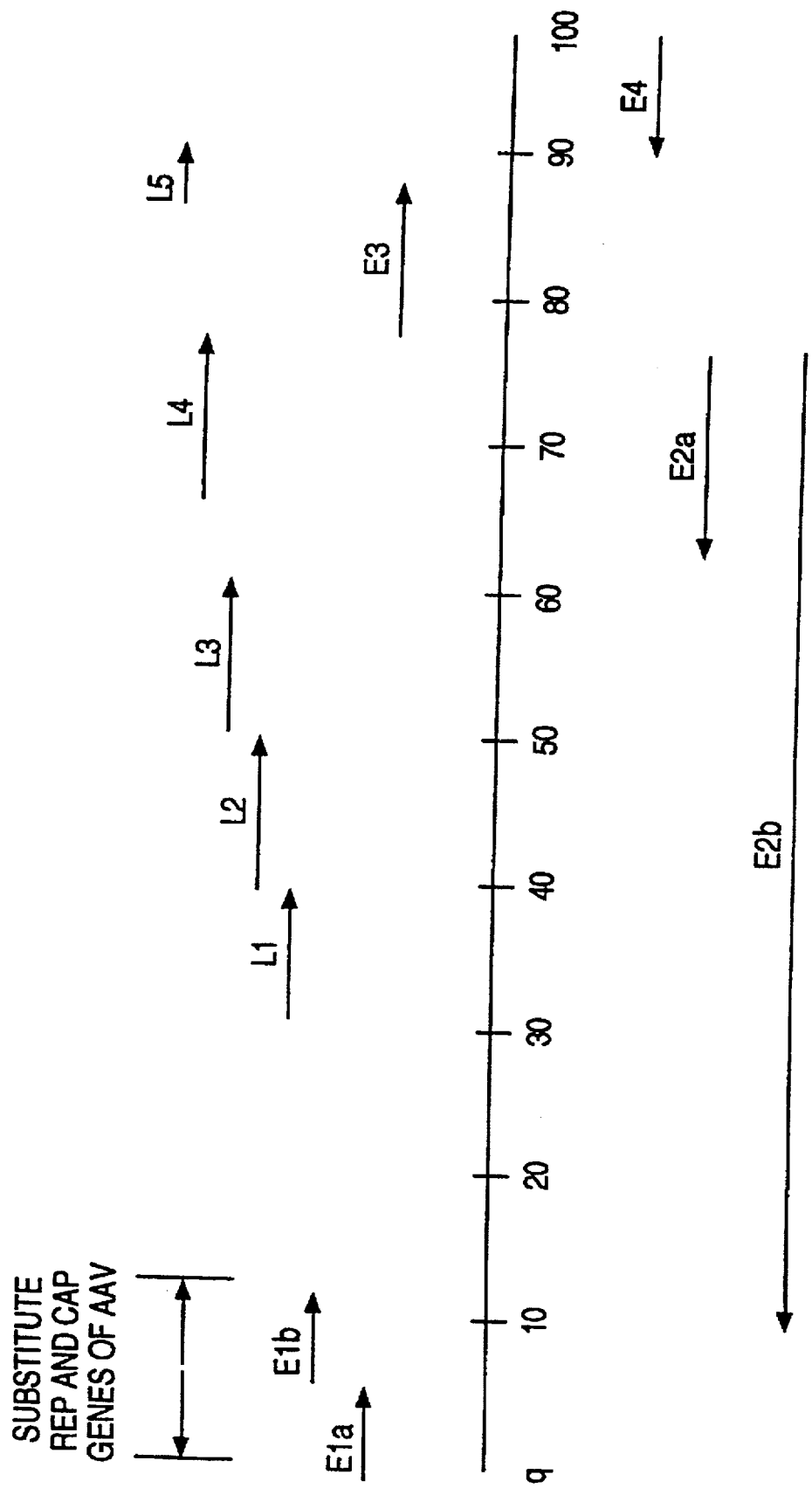
FIG. 5 depicts the construction of rep/cap adenovirus vectors by replacing the adenovirus E1a and E1b genes with the AAV rep and cap genes.
Figure 6:
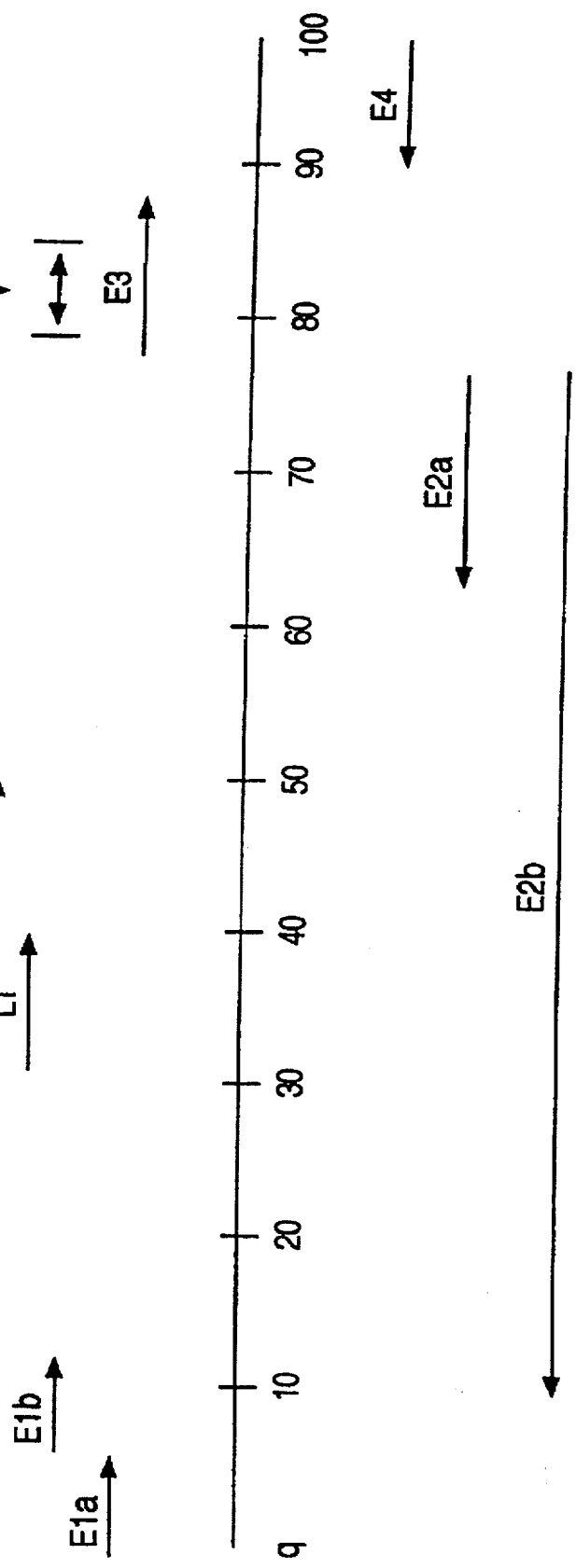
FIG. 6 depicts the construction of rep/cap adenovirus vectors by replacing the adenovirus E3 gene with the AAV rep and cap genes.

The rep/cap adenovirus vectors of the present invention are constructed by the following methods. A preferred means for constructing such vectors is by deleting the adenovirus E1a and E1b genes from the 30 kb adenovirus genome and replacing them with the AAV rep and cap genes as depicted in FIG. 5. Recombinant adenoviruses containing insertions of foreign DNA into the E1a and E1b region are well known in the art. 293 cells, which constitutively express E1a and E1b, likewise are well known and widely available. These recombinant adenovirus vectors are propagated in cells (e.g., 293 cells) which constitutively express the adenovirus E1a and E1b genes. Alternatively, as depicted in FIG. 6, the rep and cap genes replace the E3 region.

Figure 7:
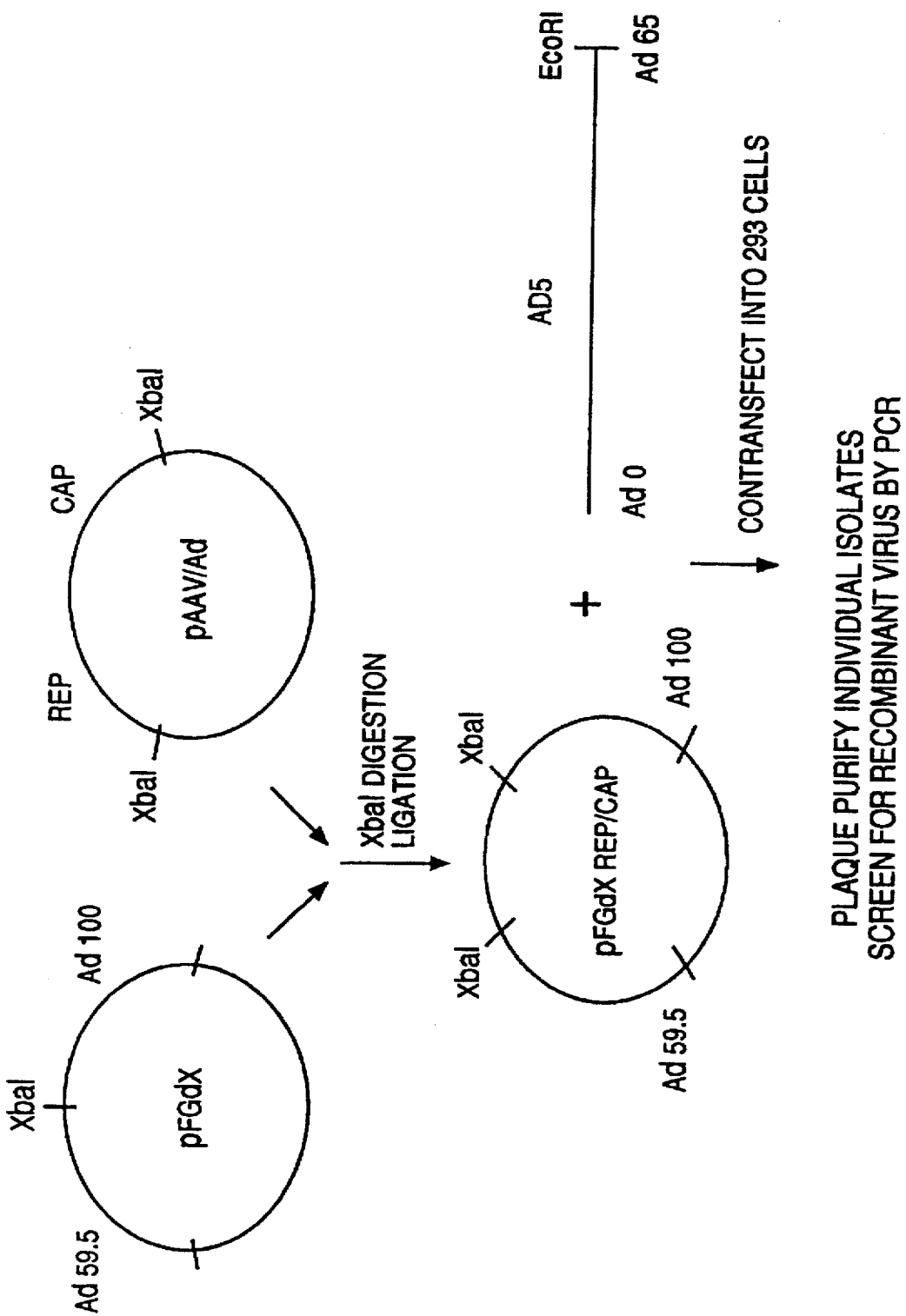
FIG. 7 shows the steps by which a recombinant rep/cap adenovirus is produced.

In one approach to the construction of a rep/cap adenovirus vector, sequences containing the rep/cap genes of AAV replace the nonessential E3 region of adenovirus by recombinant DNA techniques. For example, an XbaI fragment containing the rep/cap genes of pAAV/Ad is cloned into the XbaI site of pFGdx, which contains a portion of the adenovirus genome from map units 59.5 to 100 with a deletion of the E3 region of the virus, as shown in FIG. 7. An alternative to pFGdx is a BalI fragment from pAV2 with appropriate added XbaI linker.

Alternatively, the recombinant rep/cap adenovirus is created by cotransfecting into 293 cells pFGdx along with an EcoRI fragment of Adenovirus 5 which contains map units 1 to 60 of the virus. Plaques appearing after 1 to 14 days arise after recombination between the two transfected DNAs and replication of the recombinant rep/cap adenovirus. Individual plaques are picked, amplified and checked by PCR for the integrity of their sequence. The recombinant virus is finally tested for its ability to deliver and express the rep and cap genes in 293 cells. Expression of rep and cap genes is analyzed as described above.

An alternative means of constructing a rep/cap adenovirus vector is to replace the E1a and E1b region of adenovirus with the rep/cap sequences of AAV by recombinant cloning means. The deleted E1a and E1b functions are complemented in trans, e.g., in 293 cells, which constitutively produce E1a and E1b proteins.

Alternatively, the rep/cap sequences are inserted anywhere within adenovirus by recombinant cloning means provided that the interrupted or deleted adenovirus functions are complemented in trans in the host cell.

Figure 8:
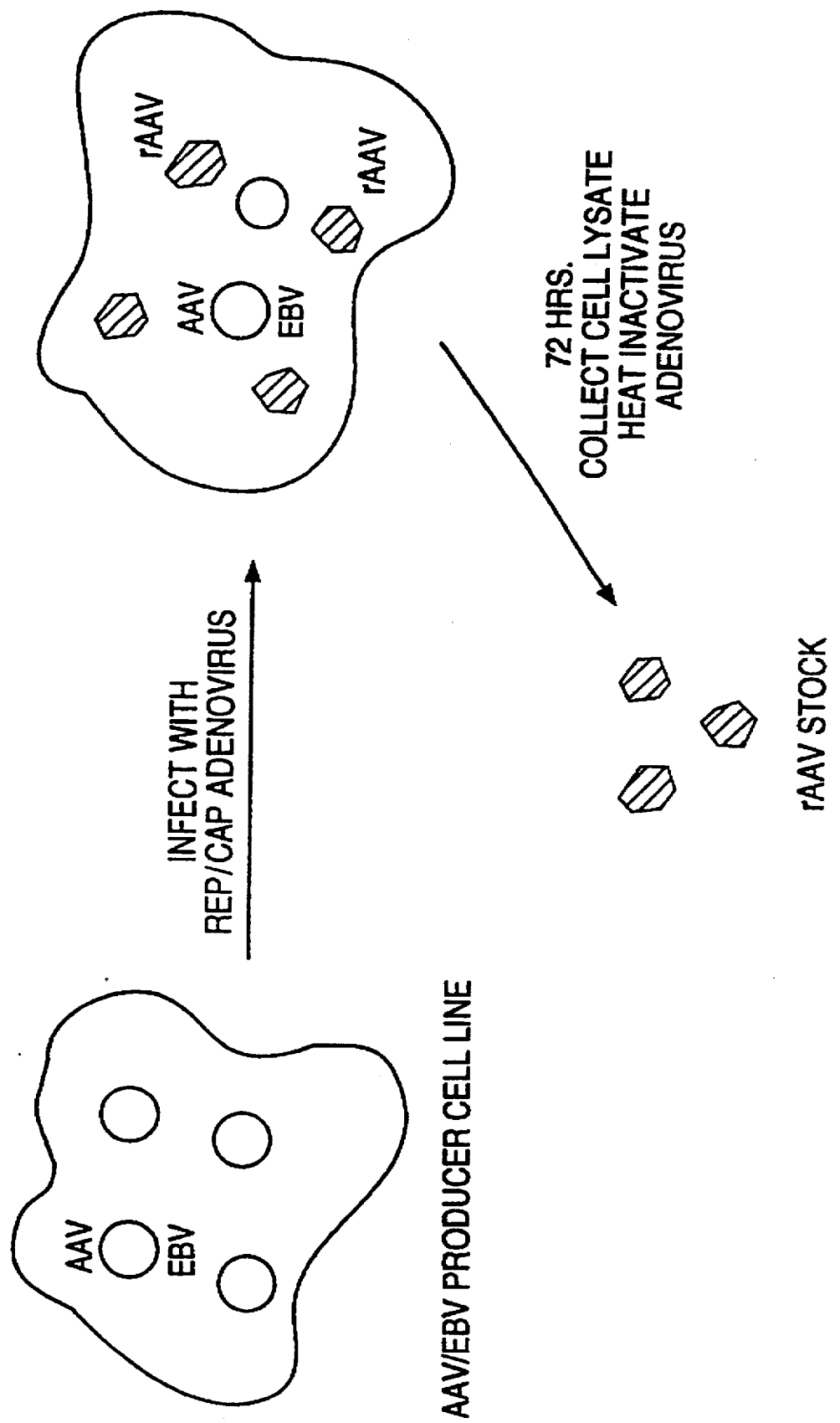
FIG. 8 shows the steps by which recombinant AAV is produced from an AAV/EBV producer cell line by infection with a rep/cap adenovirus vector.

The recombinant rep/cap adenovirus vector of the present invention is propagated in host cells, e.g., 293 cells using standard procedures. Ruether et al. (1986); and Massie et al. (1986). Expression of the rep and cap proteins from these vectors is analyzed as discussed above. The rep/cap adenovirus vectors, along with wild type adenovirus, are used to infect the AAV/EBV producer lines described above (as shown in FIG. 8), although this step may not be necessary. Again, 48 to 72 hours after infection, the infected cells are monitored for the presence of: (1) replication of rAAV genomes; (2) transducing rAAV virus; and (3) wild-type AAV.

This system for efficient delivery of the rep and cap genes offers several advantages. The rep/cap recombinant adenovirus allows infection of the producer cell line to occur simultaneously with wild type adenovirus infection. In addition, titers can be adjusted so that infection is essentially 100% efficient, preferably by employing a multiplicity of infection (m.o.i.) of between 1 to 10. Since 293 cells produce E1a and E1b, and the recombinant adenovirus provides all other adenovirus functions, such a rep/cap recombinant adenovirus may make it unnecessary to infect the producer lines with wild type adenovirus. In addition, elimination of recombinant adenovirus particles from rAAV stocks is accomplished by simple heat inactivation, exactly as is done for wild type adenovirus. Finally, incorporation of the rep and cap genes in an adenovirus vector allows one to convert essentially any cell line which can be infected by the rep/cap adenovirus vector to a cell line useful for producing rAAV.

Both approaches provide efficient means to make high titer stocks of rAAV vectors and can be used to propagate any rAAV vector while reducing the number of manipulations required to produce large quantities of virus.

EXAMPLE 8

Engineering the cellular tropisms of rAAV vectors

AAV is a dependent parvovirus that infects many cell types, yet requires a helper adenovirus for its own replication. This trait is desirable for gene therapy protocols for safety reasons. Many other parvovirus strains exhibit specific cellular tropisms. For example, B19 infects primarily erythroid cells and MVM(p) infects primarily transformed cells. While it would be possible to develop a range of vectors based on various parvoviruses having different cellular tropisms, the goal of targeted infection of specific cell types is more easily achieved by replacing the cap genes of AAV, with the cap genes of different parvoviruses, thereby conferring to the altered AAV or rAAV vector the cellular tropism of the parvovirus donating the cap gene. As used herein "different parvoviruses" means parvoviruses other than AAV. Such a system is simpler to manufacture since one is manipulating only the packaging function of a single viral genome. It also has the advantage of safely exploiting the cellular tropisms of various autonomous parvoviruses (i.e., those replication without requiring a helper adenovirus). These different parvovirus cap genes may be incorporated into the AAV vector itself, but are preferably instead stably integrated into the genome of the packaging cell line, and most preferably are incorporated into the adenovirus rep/cap vector.

A variety of parvoviruses are useful for constructing rAAV vectors having altered cellular tropism, these include, but are not limited to, B19 (erythroid cells), canine parvovirus (gut epithelium) and MVM(p) (fibroblasts). Genes encoding cap proteins of various parvoviruses confer a range of host cell specificities to the recombinant virus. Genomic maps for these parvoviruses are available, and in several cases the particular tropisms have been narrowed to particular amino acid sequences in the cap proteins. *J. Virol.*, 47:227–232 (1983); *Virology*, 184:175–186 (1991); *J. Virology*, 66:2821–2828 (1992); *J. Virol.*, 66:3118–3124 (1992); *J. Virol.*, 66:3415–3423 (1992); and *J. Virol.*, 66:6858–6867 (1992).

Figure 9:
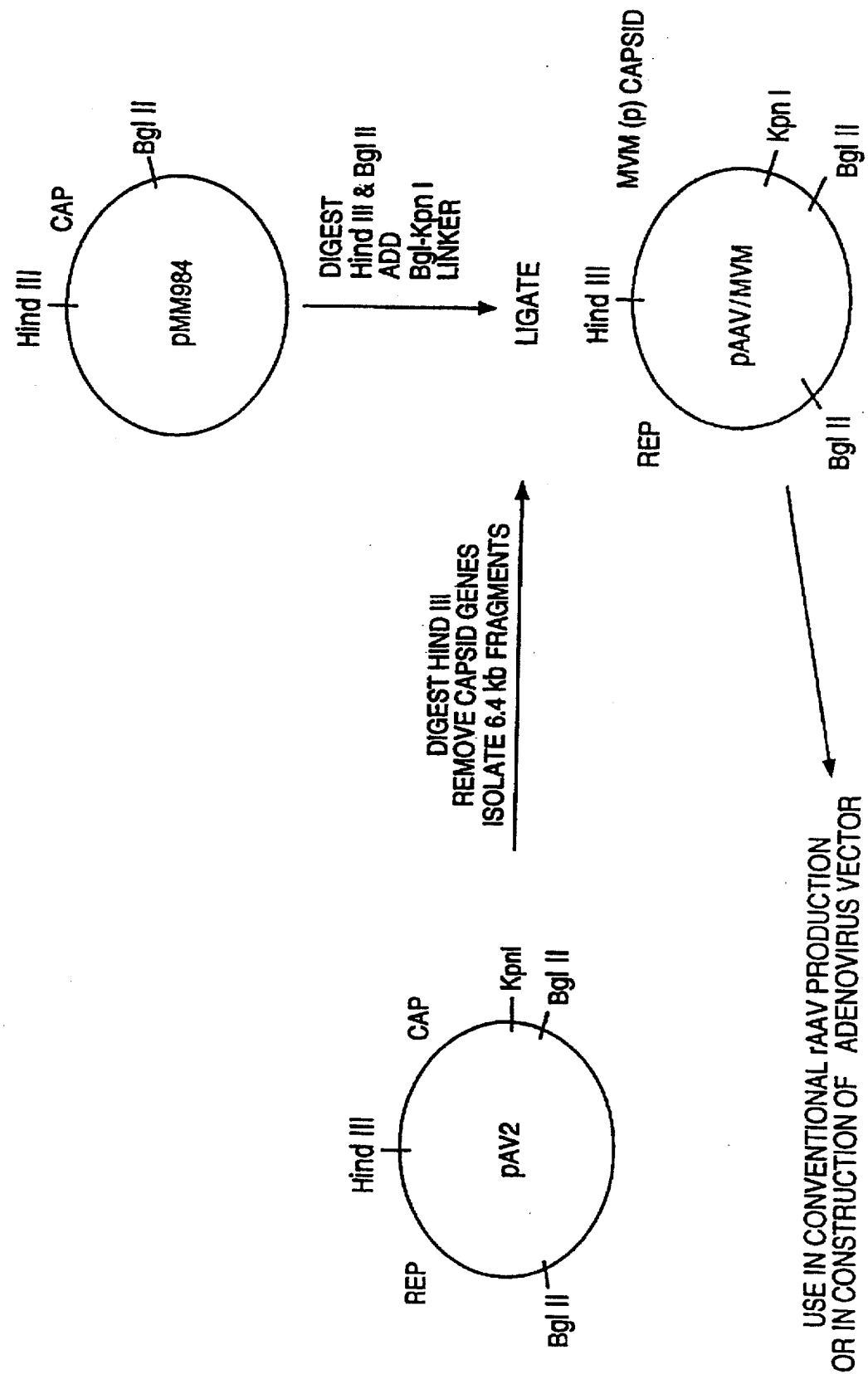
FIG. 9 shows the steps by which recombinant AAV is produced with different capsid proteins.

Such rAAV vectors are constructed by recombinant cloning methods. For example, fibrotropic rAAV vectors containing the cap genes of MVM(p) are constructed as shown in FIG. 9. The AAV cap genes from pAV2 (which has the entire genome of AAV cloned into pBR322) are deleted by digestion with HindIII and KpnI. The remaining large 6.47 kb fragment, is isolated. BglII-KpnI linkers are added (destroying the original BglII site); and the resulting fragment is ligated to the 6.4 kb AAV DNA fragment to create pAAV/MVM. After digestion with BglII, the 4.0 kb BglII fragment of pAAV/MVM, which contains the AAV rep genes and MVM(p) cap genes, is isolated. After BglII-XbaI linkers are added, the fragment is cloned into pFGdx, thereby placing the MVM(p) cap genes under the transcriptional control of the AAV cap gene promoter.

To avoid using a recombinant rep/cap adenovirus vector, pAAV/MVM is digested with BalI and the parvovirus fragment (3.8 kb) is blunt ended and cloned into the HincII site of pUC19. The resulting construct, which has the origins of replication of AAV deleted, is useful in traditional methods of rAAV production.

Note that it is not necessary, to replace all three AAV cap genes, although to do so simplifies construction of a vector with the desired cellular tropism. *J. Virol.*, 184:175–186 (1991); *J. Virol.*, 66:3415–3423 (1992); and *J. Virol.*, 62:2605–2613 (1988).

All publications and patent applications mentioned in this specification are incorporated herein by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A cell line having incorporated in its genome one or more DNA sequences, said sequences comprising:

an adeno-associated virus rep gene and an adeno-associated virus cap gene;

wherein said cell line further comprises an AAV/EBV vector, said vector comprising: an Epstein Barr nuclear antigen gene; an Epstein Barr virus latent origin of replication; and an adeno-associated virus transducing vector comprising exogenous genetic material.

2. The cell line according to claim 1 wherein said cell line is a mammalian cell line.

3. The cell line according to claim 2 wherein said cell line is a 293 cell line.

4. The cell line according to claim 2 wherein said cell line is a HeLa cell line.

5. The cell line according to claim 2 wherein said cell line is a KB cell line.

6. The cell line according to claim 2 wherein said cell line is a JW-22 cell line.

7. A method for preparing a producer cell for use in making a recombinant adeno-associated virus comprising providing a cell having one or more DNA sequences integretated into the genome of said cell, said sequences comprising an adeno-associated virus rep gene and an adeno-associated virus cap gene and introducing into said cell an AAV/EBV vector comprising: an Epstein Barr nuclear antigen gene; an Epstein Barr virus latent origin of replication; and an adeno-associated virus transducing vector comprising exogenous genetic material.

8. The method according to claim 7 further comprising infecting said packaging cell with wild-type adenovirus or herpes virus.

9. The method according to claim 7 further comprising introducing into said producer cell a vector comprising adenovirus helper functions sufficient to permit adeno-associated virus replication.

10. The method according to claim 7 further comprising introducing into said producer cell a vector comprising herpes virus helper functions sufficient to permit adeno-associated virus replication.

11. The method of claim 7 further comprising growing said producer cell in a cell growth medium.

12. The method of claim 11 further comprising introducing adenovirus to said producer cell, thereby producing recombinant adeno-associated virus.

13. The method of claim 12 further comprising isolating said recombinant adeno-associated virus.

14. A method for preparing a producer cell for use in making recombinant adeno-associated virus comprising providing a cell having one or more DNA sequences integretated into the genome of said cell, wherein expression of said sequences is under the control of an inducible promoter and said sequences comprise an adeno-associated virus rep gene and an adeno-associated virus cap gene and introducing into said cell an AAV/EBV vector comprising: an Epstein Barr nuclear antigen gene; an Epstein Barr virus latent origin of replication; and an adeno-associated virus transducing vector comprising exogenous genetic material.

* * * * *

UNITED STATES PATENT AND TRADEMARK OFFICE
CERTIFICATE OF CORRECTION

PATENT NO. : 5,691,176

DATED : November 25, 1997

INVENTOR(S) : Jane S. Lebkowski, Maureen A. McNally and Thomas B. Okarma

It is certified that error appears in the above-identified patent and that said Letters Patent is hereby corrected as shown below:

On the title page, item 73, change "Applied Immune Sciences, Inc." to --Rhone-Poulenc Rorer Pharmaceuticals Inc.--

Signed and Sealed this

Fourth Day of January, 2000

Attest:

Attesting Officer

*Acting Commissioner of Patents and Trademarks*